United States Patent
Labbe et al.

(10) Patent No.: US 9,844,665 B2
(45) Date of Patent: Dec. 19, 2017

(54) CARDIAC PACING ENERGY ENHANCEMENT

(71) Applicant: Pacesetter, Inc., Sunnyvale, CA (US)

(72) Inventors: Eric Labbe, Sunnyvale, CA (US); Will Heng Zhang Lui, Simi Valley, CA (US)

(73) Assignee: Pacesetter, Inc., Sunnyvale, CA (US)

( * ) Notice: Subject to any disclaimer, the term of this patent is extended or adjusted under 35 U.S.C. 154(b) by 68 days.

(21) Appl. No.: 14/882,130

(22) Filed: Oct. 13, 2015

(65) Prior Publication Data
US 2017/0100583 A1     Apr. 13, 2017

(51) Int. Cl.
| | | |
|---|---|---|
| A61N 1/362 | (2006.01) |
| A61N 1/08 | (2006.01) |
| A61N 1/368 | (2006.01) |
| A61N 1/39 | (2006.01) |
| A61N 1/372 | (2006.01) |
| A61N 1/05 | (2006.01) |
| A61N 1/37 | (2006.01) |
| A61N 1/378 | (2006.01) |

(52) U.S. Cl.
CPC ............... *A61N 1/08* (2013.01); *A61N 1/056* (2013.01); *A61N 1/3684* (2013.01); *A61N 1/378* (2013.01); *A61N 1/3718* (2013.01); *A61N 1/37217* (2013.01); *A61N 1/3956* (2013.01)

(58) Field of Classification Search
CPC ...... A61N 1/3718; A61N 1/37; A61N 1/3708; A61N 1/378; A61N 1/3782
See application file for complete search history.

(56) References Cited

U.S. PATENT DOCUMENTS

| | | | |
|---|---|---|---|
| 6,553,259 B2 * | 4/2003 | Mouchawar | A61N 1/3712 607/11 |
| 6,934,584 B1 * | 8/2005 | Wong | A61N 1/37 607/9 |

* cited by examiner

*Primary Examiner* — George Evanisko
(74) *Attorney, Agent, or Firm* — Theresa A. Raymer

(57) ABSTRACT

Example implantable cardiac stimulation devices, pulse generators, and methods providing enhanced cardiac pacing energy are disclosed herein. In an example, an implantable cardiac stimulation device may include a pulse generator having a pacing output node providing cardiac pacing pulses to be applied to a heart of a patient. The pulse generator may include a pulse voltage regulator that receives a pacing signal and generates cardiac pacing pulses at an output of the pulse voltage regulator according to the pacing signal. The pulse voltage regulator may receive a supply voltage to generate cardiac pacing pulses at the supply voltage, gated by the pacing signal. The pulse generator may further include routing circuitry to route the output of the pulse voltage regulator to the pacing output node of the pulse generator while the pulse generator is in a first operating mode, and to route the supply voltage, gated by the pacing signal, to the pacing output node of the pulse generator while the pulse generator is in a second operating mode.

20 Claims, 6 Drawing Sheets

CARDIAC PACING ENERGY ENHANCEMENT

FIELD OF THE INVENTION

The present invention relates to medical apparatus and methods. More specifically, the present invention relates to an implantable cardiac stimulation device and/or pulse generator providing enhanced pacing energy.

BACKGROUND OF THE INVENTION

Implantable cardiac stimulation devices, such as, for example, automatic implantable cardioverter defibrillators (AICDs) and pacemakers, have been proven reliably effective in treating a variety of arrhythmias, including cardiac arrest. However, at least one environmental circumstance has proven to be problematic for effective delivery of electrotherapy signals to the heart of the patient. More specifically, the amount of energy delivered to the heart of a patient by pacing pulses, such as those used in the treatment of cardiac arrhythmias, may be reduced significantly in the presence of strong radio frequency (RF) signals, such as those produced during an magnetic resonance imaging (MRI) scan of the patient. In at least some instances, the reduction of delivered energy may be traced to an attenuation of the pacing pulses as applied to the heart.

With the above aspects in mind, as well as others not explicitly discussed herein, various embodiments of an implantable cardiac stimulation device and pulse generator used therein, as well as methods of operating such devices, are disclosed herein.

SUMMARY

In one embodiment, an implantable cardiac stimulation device may include a pulse generator having a pacing output node, a pulse voltage regulator, and additional electronic circuitry, e.g., routing circuitry. The pacing output node may provide cardiac pacing pulses that are to be applied to a heart of a patient. The pulse voltage regulator may generate at least some of the cardiac pacing pulses at an output in accordance with a pacing signal. The pulse voltage regulator may also receive a supply voltage to generate the at least some of the cardiac pacing pulses. The additional electronic circuitry may route the output of the pulse voltage regulator to the pacing output node of the pulse generator while the pulse generator is in a first operating mode. The circuitry may also route the supply voltage, gated by the pacing signal, to the pacing output node of the pulse generator while the pulse generator is in a second operating mode. Other embodiments may include a pulse generator having the above characteristics. Further embodiments may include methods for operating an implantable cardiac stimulation device or pulse generator as described above according to a current operating state of the implantable cardiac stimulation device or pulse generator.

While multiple embodiments are disclosed, still other embodiments of the present invention will become apparent to those skilled in the art from the following detailed description, which depicts and describes illustrative embodiments of the invention. As will be realized, the invention is capable of modifications in various aspects, all without departing from the scope of the present invention. Accordingly, the drawings and detailed description are to be regarded as illustrative in nature and not restrictive.

DETAILED DESCRIPTION

The following detailed description relates to implantable cardiac stimulation devices and associated pulse generators. In one example, a pulse generator configured to provide cardiac pacing pulses may include a pulse voltage regulator that may provide the pacing pulses based on a pacing signal while the pulse generator is operating in a first (e.g., normal) operating mode. In a second (e.g., enhanced energy) mode, the pulse generator may gate a supply voltage of the pulse voltage regulator using the pacing signal and employ the gated supply voltage as the pacing pulses. In at least some examples, a voltage level of the pacing pulses during the second operating mode is higher than a voltage level of the pacing pulses during the first operating mode.

As a result of at least some of the embodiments discussed in greater detail below, the implantable cardiac stimulation device, and/or a pulse generator incorporated therein, may deliver a sufficient amount of electrical energy to the heart of the patient when placed into the enhanced energy mode while in the presence of strong RF signals, such as those produced by an MRI scanner.

Figure 1:
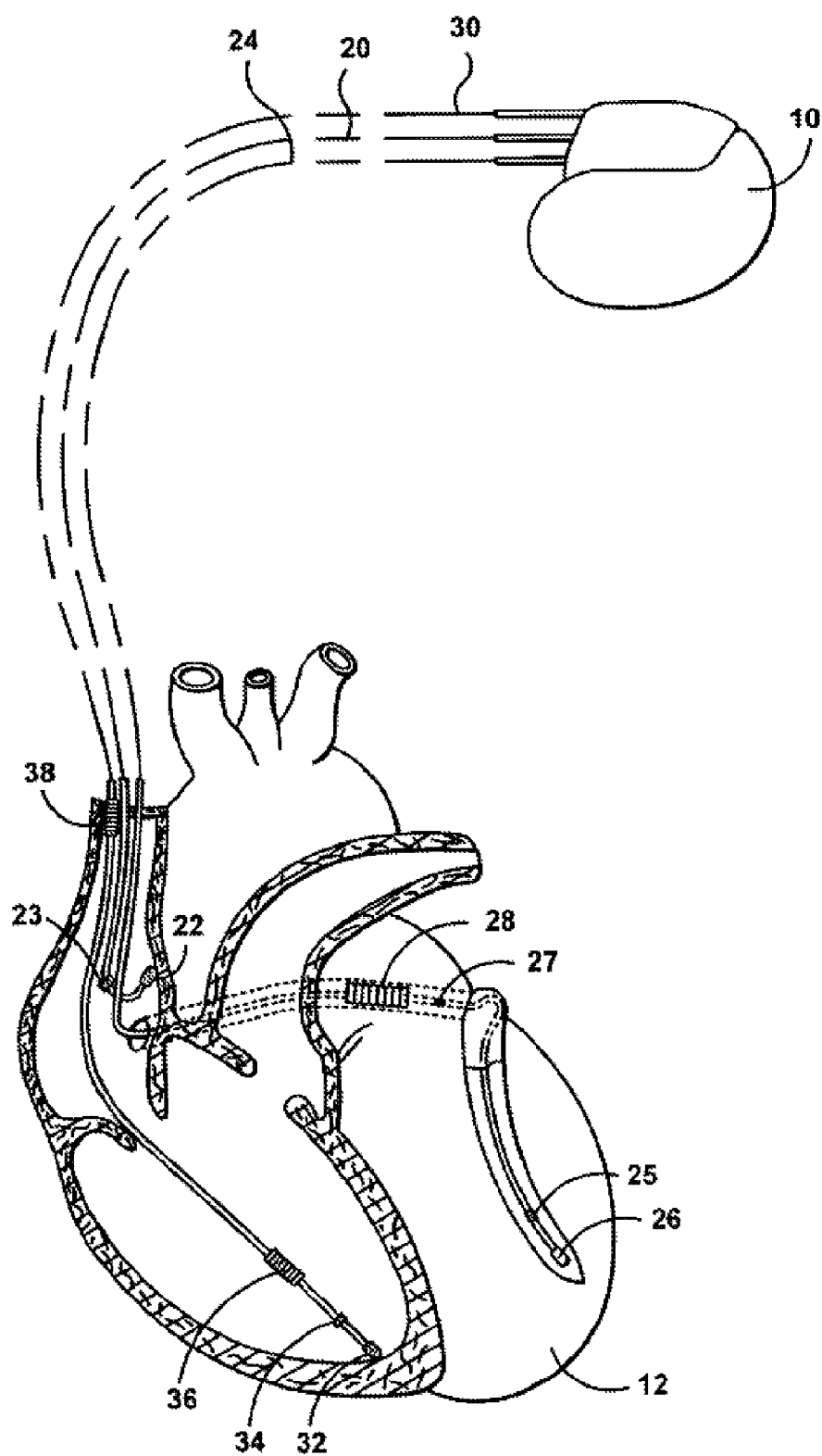
FIG. 1 is a simplified, partly cut-away view of an example implantable cardiac stimulation device in electrical communication with at least three leads implanted into a patient's heart for delivering multi-chamber stimulation and shock therapy.
Figure 2:
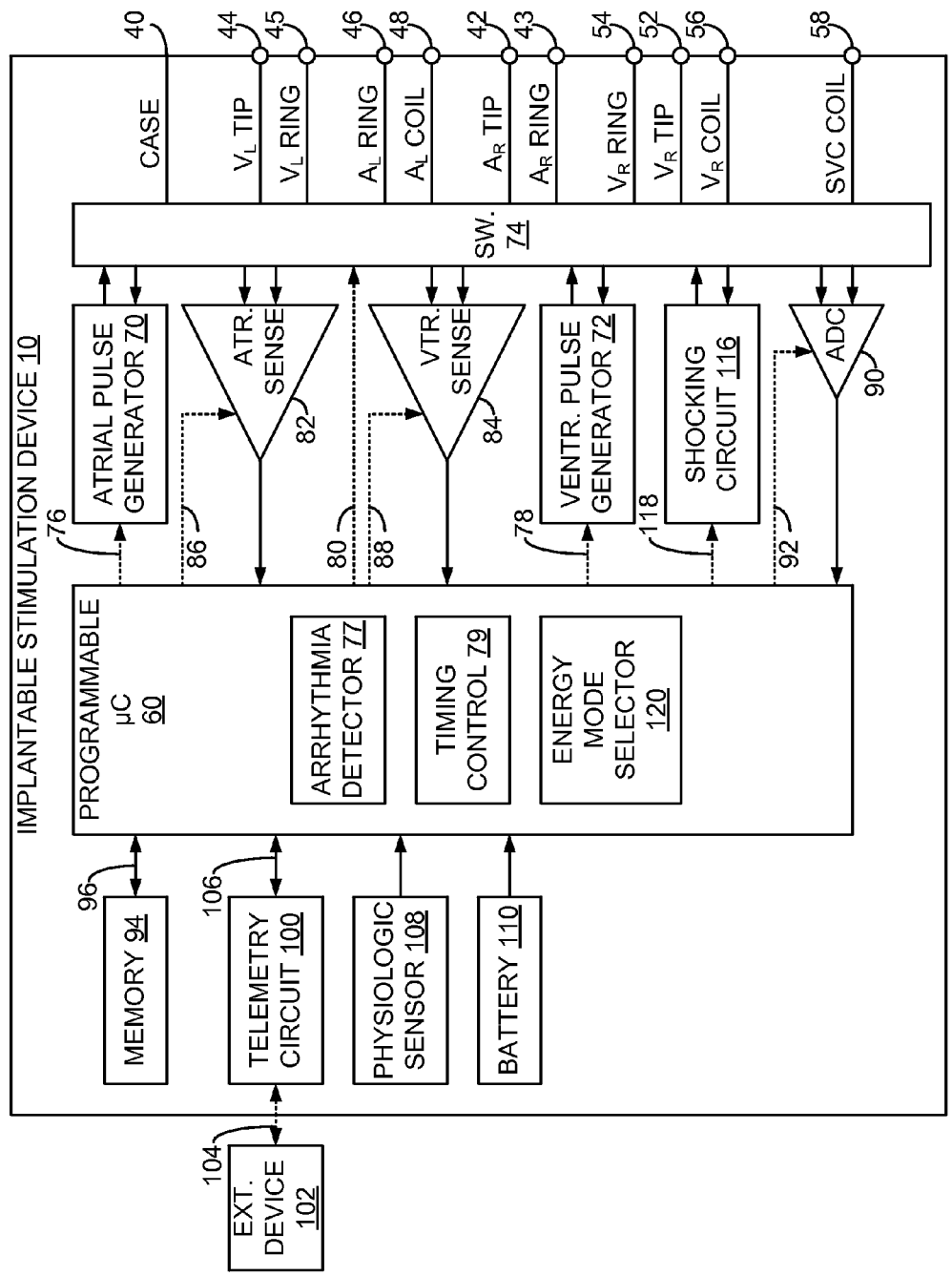
FIG. 2 is a block diagram of the example implantable cardiac stimulation device of FIG. 1, illustrating the basic elements providing pacing stimulation, cardioversion, and defibrillation in four chambers of the heart via one or more pulse generators.

An implantable cardiac stimulation device will thus be described in conjunction with FIGS. 1 and 2, in which the features included in various embodiments described hereafter could be implemented. However, numerous variations of such a device exist in which various circuits and methods discussed below can be implemented.

FIG. 1 illustrates an implantable cardiac stimulation device 10 in electrical communication with a patient's heart 12 by way of three leads 20, 24, and 30 suitable for delivering multi-chamber stimulation and/or shock therapy. To sense atrial cardiac signals and to provide right atrial chamber stimulation therapy, the device 10 may be coupled to an implantable right atrial lead 20 including at least one right atrial tip electrode 22 that may be implanted in the patient's right atrial appendage. The right atrial lead 20 may also include a right atrial ring electrode 23 to allow bipolar stimulation or sensing in combination with the atrial tip electrode 22.

To sense the left atrial and left ventricular cardiac signals and to provide left-chamber stimulation therapy, the stimulation device 10 may be coupled to a "coronary sinus" lead 24 designed for placement in the "coronary sinus region" via the coronary sinus ostium in order to place a distal electrode adjacent to the left ventricle and additional one or more electrodes adjacent to the left atrium. As used herein, the phrase "coronary sinus region" refers to the venous vasculature of the left ventricle, including any portion of the coronary sinus, great cardiac vein, left marginal vein, left posterior ventricular vein, middle cardiac vein, and/or small cardiac vein or any other cardiac vein accessible by the coronary sinus.

Accordingly, the coronary sinus lead 24 may be designed to receive atrial and/or ventricular cardiac signals, deliver left ventricular pacing therapy using at least one left ventricular tip electrode 26 for unipolar configurations or in combination with left ventricular ring electrode 25 for bipolar configurations, and/or deliver left atrial pacing therapy using at least one left atrial ring electrode 27 as well as shocking therapy using at least one left atrial coil electrode 28.

The stimulation device 10 of FIG. 1 may also be in electrical communication with the patient's heart 12 by way of an implantable right ventricular lead 30 including, in this embodiment, a right ventricular (RV) tip electrode 32, a right ventricular ring electrode 34, a right ventricular coil electrode 36, a superior vena cava (SVC) coil electrode 38, and/or so on. The right ventricular lead 30 may be inserted transvenously into the heart 12 so as to place the right ventricular tip electrode 32 in the right ventricular apex such that the right ventricular coil electrode 36 is positioned in the right ventricle and the SVC coil electrode 38 will be positioned in the right atrium and/or superior vena cava. Accordingly, the right ventricular lead 30 may be capable of receiving cardiac signals, and delivering stimulation in the form of pacing and shock therapy to the right ventricle.

FIG. 2 illustrates a simplified block diagram of the multi-chamber implantable cardiac stimulation device 10, which may be capable of treating both fast arrhythmia and slow arrhythmia with stimulation therapy, including cardioversion, defibrillation, and pacing stimulation. The particular multi-chamber device 10 shown in FIG. 2 is for illustration purposes only, and one of ordinary skill in the pertinent art could readily duplicate, eliminate, or disable the appropriate circuitry in any desired combination to provide a device capable of treating the appropriate one or more chambers with cardioversion, defibrillation, and/or pacing stimulation.

The stimulation device 10 may include a housing 40 which is often referred to as a "can," "case," or "case electrode," and which may be programmably selected to act as the return electrode for all "unipolar" modes. The housing 40 may further be used as a return electrode alone or in combination with one or more of the coil electrodes 28, 36, or 38, for defibrillation shocking purposes. The housing 40 may further include a connector having a plurality of terminals 42, 43, 44, 45, 46, 48, 52, 54, 56, and 58 (shown schematically and, for convenience, the names of the electrodes to which they are connected are shown next to corresponding terminals). As such, in order to achieve right atrial sensing and stimulation, the connector may include at least one right atrial tip terminal ($A_R$ TIP) 42 adapted for connection to the atrial tip electrode 22. The connector may also include a right atrial ring terminal ($A_R$ RING) 43 for connection to the right atrial ring electrode 23.

To achieve left chamber sensing, pacing, and/or shocking, such a connector may include a left ventricular tip terminal ($V_L$ TIP) 44, a left ventricular ring terminal ($V_L$ RING) 45, a left atrial ring terminal ($A_L$ RING) 46, and a left atrial shocking coil terminal ($A_L$ COIL) 48, that are adapted for connection to the left ventricular tip electrode 26, the left ventricular ring electrode 25, the left atrial ring electrode 27, and the left atrial coil electrode 28, respectively.

To support right ventricular sensing, pacing, and/or shocking, the connector may further include a right ventricular tip terminal ($V_R$ TIP) 52, a right ventricular ring terminal ($V_R$ RING) 54, a right ventricular shocking coil terminal ($R_V$ COIL) 56, and an SVC shocking coil terminal (SVC COIL) 58, which are adapted for connection to the right ventricular (RV) tip electrode 32, the RV ring electrode 34, the RV coil electrode 36, and the SVC coil electrode 38, respectively.

At the core of the stimulation device 10 is a programmable microcontroller 60 that may control the various modes of stimulation therapy. The microcontroller 60 may include a microprocessor or equivalent control circuitry designed specifically for controlling the delivery of stimulation therapy, and may include random access memory (RAM) and/or read-only memory (ROM), logic and timing circuitry, state machine circuitry, and/or input/output (I/O) circuitry. Further, the microcontroller 60 may have the ability to process or monitor various input signals (data) as controlled by a program code stored in a designated block of memory.

In the embodiment of FIG. 2, the stimulation device 10 includes an atrial pulse generator 70 and a ventricular pulse generator 72 that may generate stimulation pulses for delivery by the right atrial lead 20, the right ventricular lead 30, and/or the coronary sinus lead 24 via an electrically configurable switch 74. To provide the stimulation therapy in each of the four chambers of the heart 12, the atrial pulse generator 70 and the ventricular pulse generator 72 may include, for example, dedicated pulse generators, independent pulse generators, multiplexed pulse generators, and/or shared pulse generators. The atrial pulse generator 70 and the ventricular pulse generator 72 may be generally controlled by the microcontroller 60 via appropriate control signals 76 and 78, respectively, to trigger or inhibit the stimulation pulses, as well as place the atrial pulse generator 70 and/or the ventricular pulse generator 72 in an enhanced energy mode, as is described in greater detail below in conjunction with FIGS. 3 through 6.

The microcontroller 60 may further include timing control circuitry 79, which may be used to control timing of the stimulation pulses such as, for example, pacing rate, atrioventricular (AV) delay, atrial interchamber (A-A) delay, and/or ventricular interchamber (V-V) delay. Such timing control circuitry 79 may also be used to keep track of the timing of refractory periods, noise detection windows, evoked response windows, alert intervals, marker channel timing, and so on.

The switch 74 may include a plurality of switches for connecting the desired electrodes to the appropriate I/O circuits, thereby providing complete electrode programmability. Accordingly, the switch 74, in response to a control signal 80 from the microcontroller 60, may determine the polarity of the stimulation pulses (e.g., unipolar, bipolar, cross-chamber, and the like) by selectively opening and closing the appropriate combination of switches. Atrial sensing circuits 82 and ventricular sensing circuits 84 may also be selectively coupled to the right atrial lead 20, coronary sinus lead 24, and the right ventricular lead 30 through the switch 74 for detecting the presence of cardiac activity in each of the four chambers of the heart 12.

Accordingly, the atrial sensing circuit 82 and the ventricular sensing circuit 84 may include dedicated sense amplifiers, multiplexed amplifiers, and/or shared amplifiers. The switch 74 determines the "sensing polarity" of the cardiac signal by selectively closing the appropriate switches of the switch 74. In this way, the clinician may program the sensing polarity independent of the stimulation polarity.

Each of the atrial and ventricular sensing circuits 82, 84 may employ one or more low-power precision amplifiers with programmable gain, automatic gain, and/or sensitivity control, one or more band-pass filters, and/or a threshold detection circuit, to selectively sense the cardiac signal of interest. The automatic sensitivity control may enable the stimulation device 10 to deal effectively with the difficult problem of sensing the low amplitude signal characteristics of atrial or ventricular fibrillation.

The outputs of the atrial sensing circuit 82 and ventricular sensing circuits 84 may be connected to the microcontroller 60 for triggering or inhibiting the atrial and ventricular pulse generators 70 and 72, respectively, in a demand fashion in response to the absence or presence of cardiac activity, respectively, in the appropriate chambers of the heart 12. The atrial and ventricular sensing circuits 82 and 84, in turn, may receive control signals over signal lines 86 and 88 from the microcontroller 60 for controlling the gain, threshold, polarization charge removal circuitry, and the timing of any blocking circuitry coupled to the inputs of the atrial and ventricular sensing circuits 82 and 84.

For arrhythmia detection, the stimulation device 10 may include an arrhythmia detector 77 that utilizes the atrial and ventricular sensing circuits 82 and 84 to sense cardiac signals for determining whether a rhythm may be physiologic or pathologic. As used herein, "sensing" generally refers to the process of noting an electrical signal, while "detection" generally refers to the step of confirming the sensed electrical signal as the signal being sought by the detector. As an example, "detection" applies to the detection of both proper rhythms (i.e., "P wave" or "R wave") as well as improper dysrhythmias including arrhythmia and bradycardia (e.g., detection of the absence of a proper rhythm).

The timing intervals between sensed events (e.g., P-waves, R-waves, and/or depolarization signals associated with fibrillation which are sometimes referred to as "F-waves" or "Fib-waves") may then be classified by the arrhythmia detector 77 by comparing them to a predefined rate zone limit (e.g., bradycardia, normal, low-rate ventricular tachycardia, high-rate ventricular tachycardia, fibrillation rate zones, and so on) and various other characteristics (e.g., sudden onset, stability, morphology, information from one or more physiologic sensors 108, and so on) to determine the type of remedial therapy required (e.g., bradycardia pacing, anti-tachycardia stimulation, cardioversion shocks, and/or defibrillation shocks, collectively referred to as "tiered therapy").

Cardiac signals may also be applied to the inputs of a data acquisition system 90 which is depicted as an analog-to-digital converter (ADC) for simplicity of illustration. The data acquisition system 90 may be configured to acquire intracardiac electrogram (EGM) signals, convert the raw analog data into digital signals, and store the digital signals for later processing and/or telemetric transmission (e.g., via wireless signals 104) to an external device 102 by way of telemetry circuit 100. The external device 102 may also be utilized to configure the stimulation device 10 via the telemetry circuit 100, such as, for example, to place the atrial pulse generator 70 and/or the ventricular pulse generator 72 (and/or the stimulation device 10) in an enhanced or non-enhanced energy delivery mode, described below in conjunction with FIGS. 3 through 6. Such a data acquisition system 90 may be coupled to the right atrial lead 20, the coronary sinus lead 24, and/or the right ventricular lead 30 through the switch 74 to sample the cardiac signals across any pair of desired electrodes.

The microcontroller 60 may further be coupled to a memory 94 by a suitable data/address bus 96, wherein the programmable operating parameters used by the microcontroller 60 may be stored and modified, as required, so as to customize the operation of the stimulation device 10 to suit the needs of particular patients. Such operating parameters may define, for example, stimulation pulse amplitude, pulse duration, polarity of electrodes, rate, sensitivity, automatic features, arrhythmia detection criteria, and/or the amplitude, shape of waves, and/or vector of each stimulation pulse to be delivered to the patient's heart 12 within each respective tier of therapy.

The stimulation device 10 may additionally include a power source that may be illustrated as a battery 110 for providing operating power to all the circuits of FIG. 2. For the stimulation device 10 employing shocking therapy, the battery 110 may be capable of operating at low current drains for long periods of time, such as, for example, less than 10 microamps (µA), and may also be capable of providing high-current pulses when the patient requires a shock pulse (e.g., in excess of 2 A at voltages above 2 volts (V) for periods of 10 seconds (s) or more).

In accordance with various embodiments disclosed below, the microcontroller 60 may also include an energy mode selector 120 to select whether the atrial pulse generator 70 and/or the ventricular pulse generator 72 (or, more generally, the implantable stimulation device 10) is to be operated currently in a "normal" or "enhanced" pacing energy mode. In one example, the microcontroller 60 may receive a signal from the external device 102 via the telemetry circuit 100 indicating an explicit selection of the particular pacing energy mode to employ. In some embodiments, the energy mode selector 120 may receive information from the atrial and ventricular sensing circuits 82, 84, the ADC 90, and/or the like to determine the particular pacing energy mode to use.

The microcontroller 60, in one embodiment, may perform the functions of the arrhythmia detector 77, the timing control 79, the energy mode selector 120, and/or other functions described herein by executing instructions stored in the memory 94. Accordingly, the microcontroller 60 may operate as the arrhythmia detector 77 for periods of time, the timing control 79 for other periods of time, and so on. In some examples, the microcontroller 60 may operate as these particular functional blocks in a concurrent or parallel manner.

Figure 3:
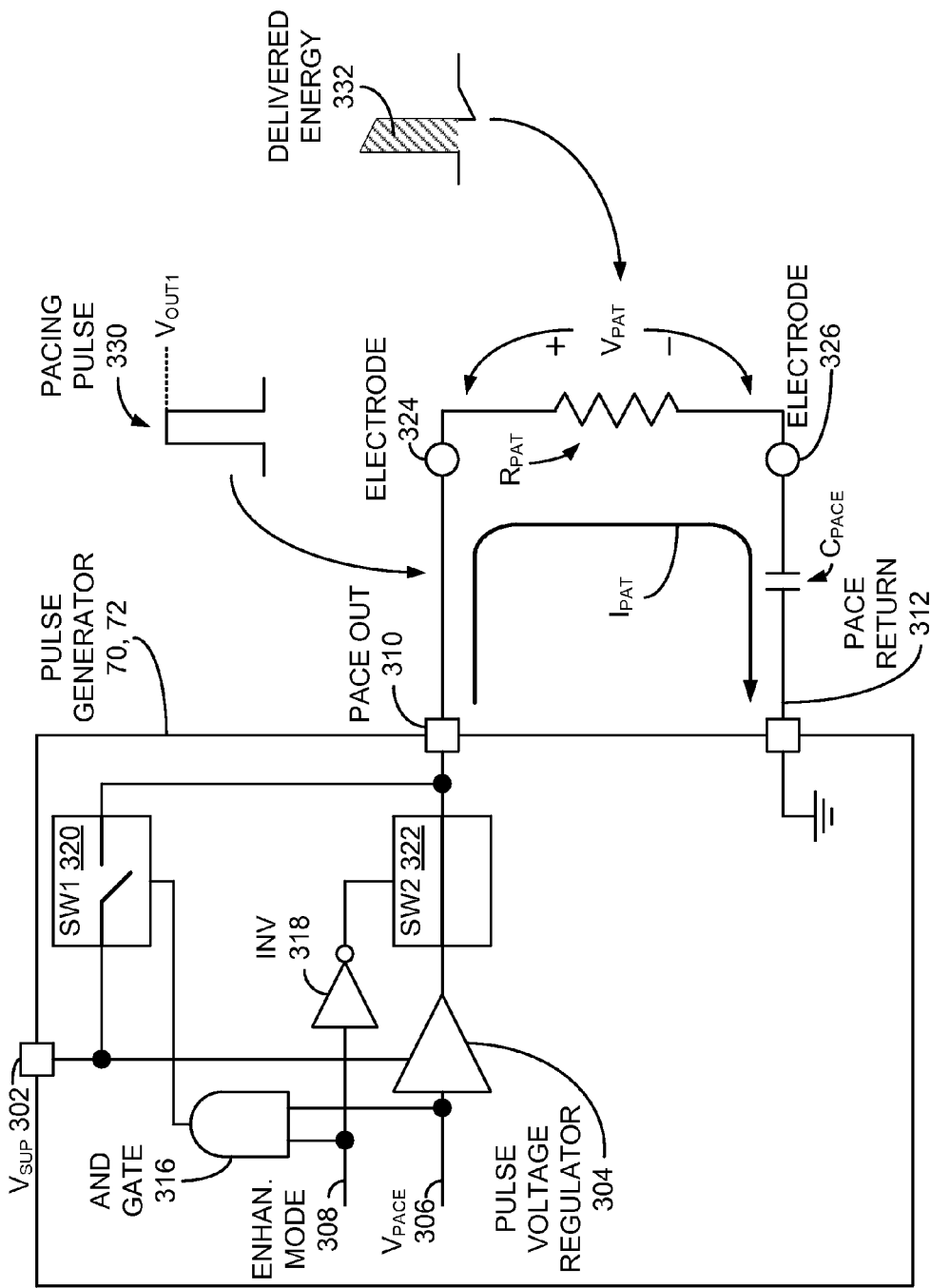
FIG. 3 is a partial block diagram of an example pulse generator employable in the implantable cardiac stimulation device of FIG. 2 being operated in a non-enhanced energy mode in the absence of an RF signal.
Figure 4:
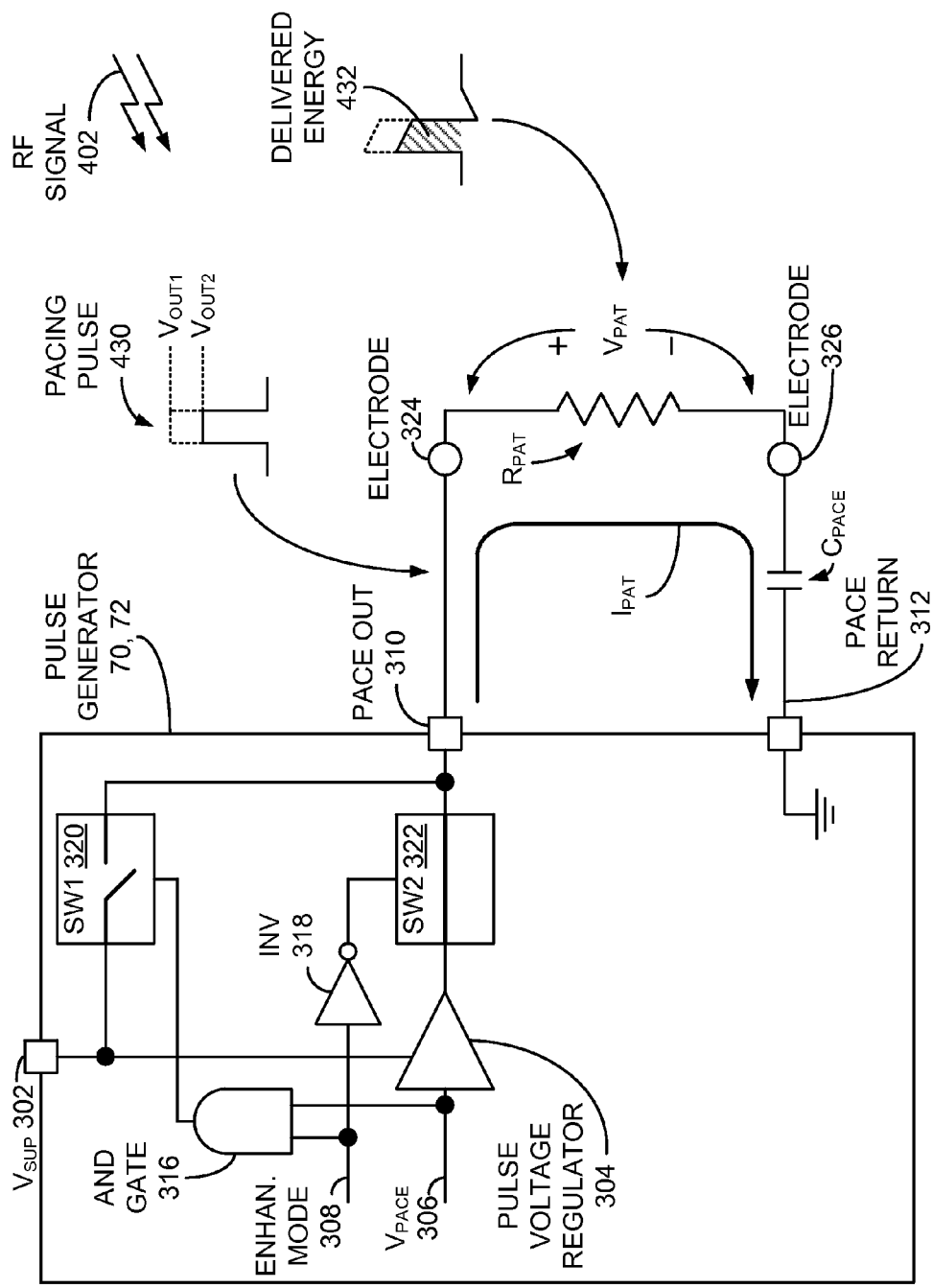
FIG. 4 is a partial block diagram of an example pulse generator employable in the implantable cardiac stimulation device of FIG. 2 being operated in a non-enhanced energy mode in the presence of an RF signal.
Figure 5:
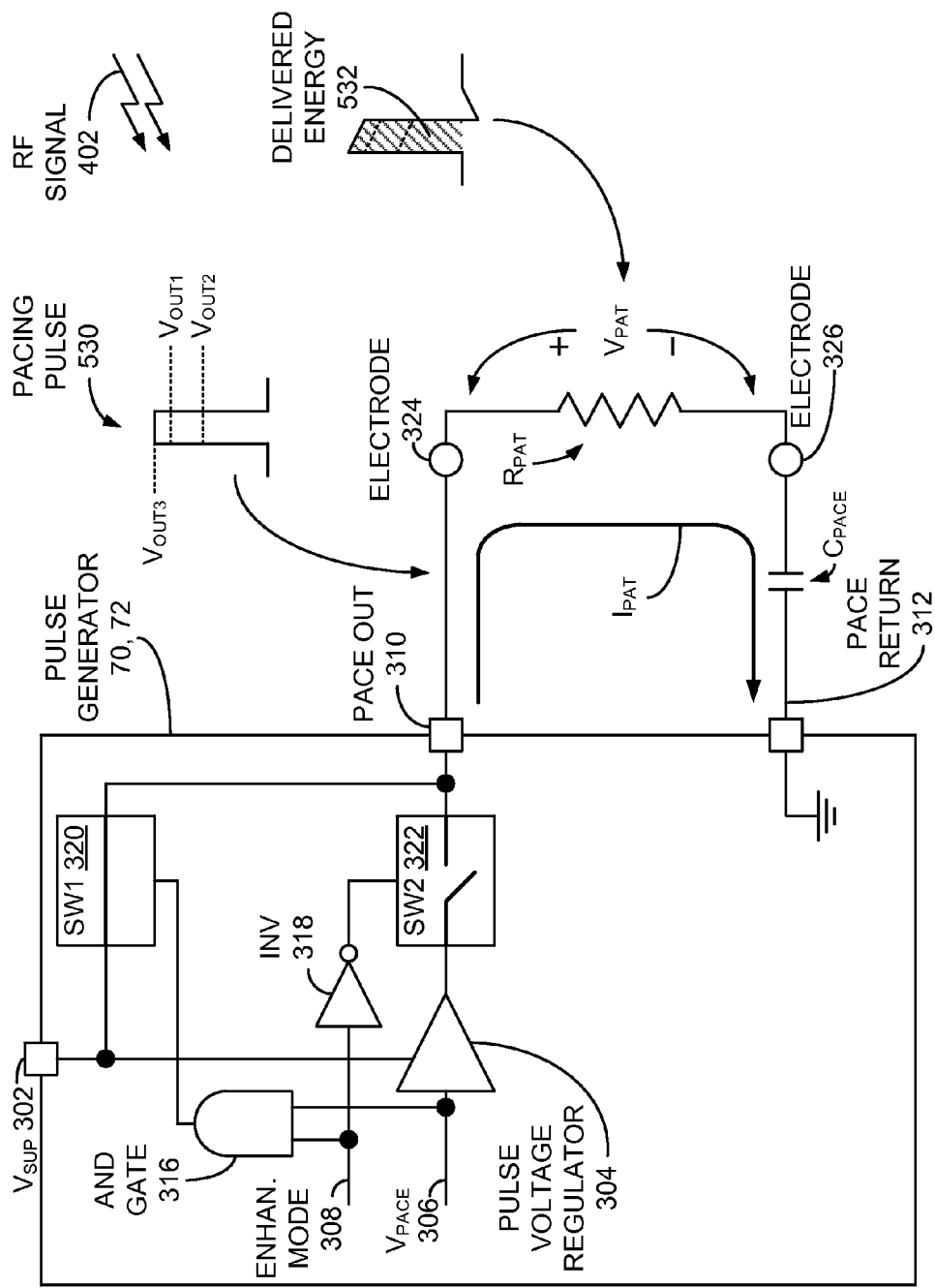
FIG. 5 is a partial block diagram of an example pulse generator employable in the implantable cardiac stimulation device of FIG. 2 being operated in an enhanced energy mode in the presence of an RF signal.

FIGS. 3 through 5 depict a particular embodiment of the atrial pulse generator 70 and/or the ventricular pulse generator 72 which may incorporate a circuit capable of operating in the two pacing modes mentioned above: a "normal mode," in which pacing pulses produced at an electrode (e.g., one or more of the right atrial tip electrode 22, the right atrial ring electrode 23, the left ventricular tip electrode 26, the left ventricular ring electrode 25, the left atrial ring electrode 27, the right ventricular tip electrode 32, and the right ventricular ring electrode 34) are voltage-regulated under the control of the microcontroller 60, and an "enhanced mode," in which the pacing pulses are driven by a supply voltage provided to the pulse generator 70, 72 and/or a voltage regulator incorporated therein to yield a greater amount of energy to the heart 12 of the patient. In some embodiments, the enhanced mode may be selected in high-energy radio-frequency (RF) environments, such as what may be encountered by the patient during a magnetic resonance imaging (MRI) scan.

More specifically, the RF signals produced by an MRI scan may induce a voltage, and a current associated therewith, within the cardiac leads coupling the electrodes to the stimulation device 10, possibly causing attenuation or cancellation in the pacing pulse being delivered to the heart 12 during normal operation of the stimulation device 10. This attenuation may result in less energy being delivered to the heart 12 than what was intended, thus possibly causing a lack of therapeutic benefit to the patient while the RF signals are present. In environments in which the RF signals include relatively long signal bursts (e.g., 10 milliseconds (ms)), the entire width of one or more pacing pulses may be attenuated such that an ineffective amount of energy is transferred to the heart 12 for pacing purposes. If, instead, the RF signals include relatively short signal bursts (e.g., 200 microseconds (μs)), only a portion of a pacing pulse may be attenuated, potentially resulting in the pacing pulse appearing as two separate pulses, thus possibly causing undesirable irregular pacing activity of heart 12.

FIG. 3 is a partial block diagram of an example pulse generator 70, 72 employable in the implantable cardiac stimulation device 10 of FIG. 2 being operated in the normal (e.g., non-enhanced) energy mode in the absence of an RF signal. In some embodiments, the pulse generator 70, 72 may be an integrated circuit in which other functional blocks depicted in FIG. 2 may or may not be incorporated. As shown, the pulse generator 70, 72 may include a pulse voltage regulator 304 that receives a pacing signal ($V_{PACE}$) 306 as input from, for example, the microcontroller 60 (e.g., control signal 76, 78), and produces a pacing pulse 330 in response by way of a pacing output node 310 of the pulse generator 70, 72, with the pacing pulse 330 being carried via a lead (e.g., lead 20, 24, or 30 of FIG. 1) and an electrode 324 to the heart 12. In at least some examples, a pacing pulse 330 is generated for each pulse of the pacing signal 306, with the pacing pulse 330 substantially duplicating the timing and duration of its corresponding pulse of the pacing signal 306, but at a voltage controlled by the pulse voltage regulator 304. The pacing pulse 330 is thus applied to at least a portion of the patient's heart 12, represented in FIG. 3 as a patient resistance or impedance $R_{PAT}$, resulting in a patient voltage $V_{PAT}$ and an electrical current $I_{PAT}$. The electrical current $I_{PAT}$ may then be returned to the pulse generator 70, 72 via a second electrode 326 to a pace return 312 of the pulse generator 70, 72. In some embodiments, the second electrode 326 may be coupled with the pace return 312 via a pace capacitor $C_{PACE}$.

In some examples, the pulse voltage regulator 304 may be configured via the control signal 76, 78 of the microcontroller 60 to produce a particular voltage level for the pacing pulse 330 in response to receiving the pacing signal 306, or may generate the particular voltage level for the pacing pulse 330 in response to a particular voltage level of the pacing signal 306.

To produce the desired voltage level for the pacing pulse 330, the pulse voltage regulator 304 uses a supply voltage ($V_{SUP}$) 302 provided to the pulse generator 70, 72 that is generally higher than the voltage levels producible at the output of the pulse voltage regulator 304. Further, the pulse voltage regulator 304 may be limited in terms of the amount of electrical current that may be delivered at a particular pacing pulse 330 output level compared to the supply voltage 302. The supply voltage 302 may be provided by a battery (e.g., the battery 110 of FIG. 2) or some other voltage supply. In at least some examples, the supply voltage 302 may be directly proportional to the voltage of the battery 110 of the stimulation device 10. Also, the supply voltage 302 may be provided directly by the battery 110, or may be provided by a voltage regulator, direct-current-to-direct-current (DC-to-DC) converter, or other circuit not explicitly shown in FIGS. 3 through 5 that transforms a voltage of the battery 110 to the supply voltage 302.

As shown in FIG. 3 (and thereafter in FIGS. 4 and 5), the pulse generator 70, 72 may be configured in the normal or enhanced energy mode by way of two switches SW1 320 and SW2 322 and assorted logic circuitry, collectively referred to herein as routing circuitry. In the specific examples of FIGS. 3 through 5, the logic circuitry may include an AND gate 316 and an inverter (INV) 318. However, in other examples, circuitry other than the AND gate 316, the inverter INV 318, SW1 320, and SW2 322 may be employed to provide the same or similar functionality as that discussed herein.

In FIGS. 3 through 5, an enhanced mode signal 308 may be received as one of the control signals 76, 78. The state of the enhanced mode signal 308 determines whether the pulse generator 70, 72 operates in a normal or enhanced energy mode. In one example, the energy mode selector 120 provides the enhanced mode signal 308. In the specific example of FIG. 3, the enhanced mode signal 308 is inactive, thus causing the output of the AND gate 316 to remain low regardless of the state of the pacing signal 306, thus causing switch SW1 320 to open. In addition, the inactive state of the enhanced mode signal 308, by virtue of the INV 318, causes switch SW2 322 to close. Consequently, the output of the pulse voltage regulator 304 is connected to the pacing output node 310, resulting in the pacing pulse 330 generated by the pulse voltage regulator 304 to be coupled via the electrode 324 to the heart 12 of the patient.

In the example of FIG. 3, no RF signals are impinging upon the leads and electrodes 324, 326, resulting in a non-attenuated voltage level of $V_{OUT1}$ for the pacing pulse 330. As a result of the pacing pulse 330, the patient voltage $V_{PAT}$ is not attenuated or cancelled, and the resulting energy 332 delivered to the heart 12 is sufficient to provide the intended therapeutic benefit.

FIG. 4 is a partial block diagram of the example pulse generator 70, 72 being operated in the normal or non-enhanced energy mode in the presence of an RF signal 402. In one example, the RF signal 402 is a 64 megahertz (MHz) signal produced during an MRI scan by an MRI scanner providing a magnetic flux density of 1.5 Tesla (T). However, other types of machines or devices may produce RF signals 402 at the same or different frequencies and strengths.

In the presence of the RF signal 402, the output level of the pacing pulse 430 produced at the pacing output node 310 of the pulse generator 70, 72 may be reduced to $V_{OUT2}$, shown to be significantly less the $V_{OUT1}$. Such attenuation may result from an RF current induced in the leads coupling the electrodes 324 and 326 to the stimulation device 10. In turn, the reduced pacing pulse 430 results in less energy 432 being delivered to the patient as a result of the RF signal 402 being present, presuming the output of the pulse voltage regulator 304 is approximately the same as in the example of FIG. 3.

Generally, increasing the output voltage level of pulse voltage regulator 304 is insufficient to overcome the attenuation imposed by a strong RF signal 402 due to typical limitations in the electrical current or power that may be generated by the pulse voltage regulator 304. In other words, the pulse voltage regulator 304 may not possess sufficient signal driving capability to reduce the attenuation imposed on the pacing pulse 430 by the RF signal 402, even when the pulse voltage regulator 304 is instructed to increase the voltage level of the pacing pulse 430, such as by increasing the voltage level of the pacing signal 306. For example, the pulse voltage regulator 304 may not be capable of responding linearly to an increase in the voltage level of the pacing signal 306 with a corresponding increase in voltage of the pacing pulse 430 during such RF interference. Moreover, depending on the driving capability of the pulse voltage regulator 304, the strength of the RF signal 402, and/or other factors, the amount of attenuation experienced by the pacing pulse 430 may be essentially unchanged regardless of the voltage level of the input pacing signal 306 or any other effort to increase the output voltage of the pulse voltage regulator 304. However, embodiments of the pulse generator 70, 72 disclosed herein provide an enhanced energy mode to produce a pacing pulse 430 that is not restricted by operating characteristics of the pulse voltage regulator 304.

FIG. 5 is a partial block diagram of the example pulse generator 70, 72 being operated in an enhanced energy mode in the presence of the RF signal 402. In this particular example, to set the pulse generator 70, 72 in the enhanced energy mode, the microcontroller 60 may activate the enhanced mode signal 308, thus causing the output of the inverter INV 318 to open the switch SW2 322, thereby disconnecting the output of the pulse voltage regulator 304 from the pacing output node 310 of the pulse generator 70, 72. Further, the activated enhanced mode signal 308, via the AND gate 316, causes the pacing signal 306 to close the switch SW1 320 so that the supply voltage ($V_{SUP}$) 302 of the pulse voltage regulator 304 is passed to the pacing output node 310 (and, accordingly, to the heart 12 of the patient via the electrode 324) during the pulses of the pacing signal 306, thus "gating" the supply voltage 302 using the pacing signal 306. The resulting pacing pulse 530 applied to the electrode 324 may thus possess a higher voltage level $V_{OUT3}$ than either $V_{OUT}$ of FIG. 3 or $V_{OUT2}$ of FIG. 4 due to the voltage not being subjected to losses through the pulse voltage regulator 304. Additionally, due to the ability of the supply voltage 302 to provide more power and/or current than what is possible via the pulse voltage regulator 304, as described above, the voltage level $V_{OUT3}$ of the pacing pulse 530, as well as the higher associated energy 532 delivered to the patient, may be maintained in the presence of a strong RF signal 402.

Figure 6:
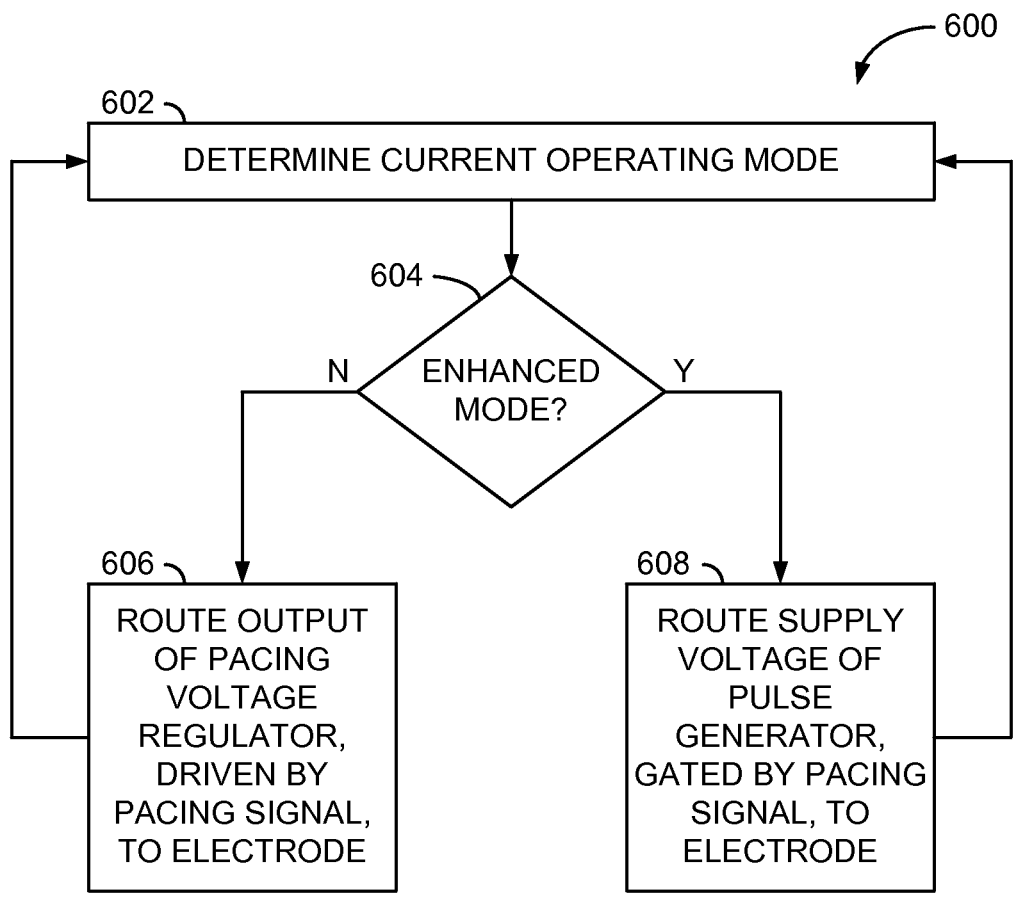
FIG. 6 is a flow diagram of an example method of operating a pulse generator of the implantable cardiac stimulation device of FIG. 2 in an enhanced energy mode and a non-enhanced energy mode.

FIG. 6 is a flow diagram of an example method 600 of operating a pulse generator of an implantable stimulation device in a normal energy mode and an enhanced energy mode. While the method 600 is described below within the context of the pulse generator 70, 72 of the implantable stimulation device 10 of FIG. 2, other circuits or systems may employ the method 600 in other examples.

In the method 600, the current operating mode of the pulse generator 70, 72 may be determined (operation 602), such as by way of the current state of the enhanced energy mode signal 308 from the microcontroller 60. If the current operating mode is not enhanced mode (e.g., the enhanced energy mode signal 308 is inactive) (operation 604), the output of the pulse voltage regulator 304, driven by the pacing signal 306, is routed to the electrode 324 (operation 606) (or, in other words, applied across the electrodes 324 and 326). If, instead, the current operating mode is enhanced mode (e.g., the enhanced energy mode signal 308 is active) (operation 604), the supply voltage 302 of the pulse generator 70, 72 (or the pulse voltage regulator 304), gated by the pacing signal 306, is routed to the electrode 324 (operation 608) (or, in other words, applied across the electrodes 324 and 326).

In one example, an operator of an external device (e.g., the external device 102) may transmit one or more wireless signals 104 to telemetry circuit 100 to set the enhanced energy mode via the energy mode selector 120 of the microcontroller 60 prior to the patient being scanned by an MRI scanner. By operating the stimulation device 10 in the enhanced mode, RF signals generated during the scan may not attenuate or cancel the pacing signals being applied to the heart 12 of the patient, thus providing effective electrotherapy to the patient under potentially adverse circumstances. After the scan has been completed, the operator may then employ the external device 102 to revert the operating mode of the stimulation device 10 back to the normal, non-enhanced energy mode to allow normal voltage regulation of the pacing pulses via the pulse voltage regulator 304 of the pulse generator 70, 72. However, other circumstances in which RF signals may be applied to the patient may also be candidates for the use of the enhanced energy mode.

Those skilled in the art will understand and appreciate that various modifications not explicitly described above may be made to the present disclosure and still remain within the scope of the present invention. Moreover, although the present invention has been described with reference to preferred embodiments, persons skilled in the art will recognize that changes may be made in form and detail without departing from the scope of the present invention.

What is claimed is:

1. An implantable cardiac stimulation device for stimulating a heart of a patient, the implantable cardiac stimulation device comprising:
   a pulse generator comprising:
      a pacing output node configured to provide cardiac pacing pulses to the heart of the patient;
      a pulse voltage regulator configured to:
         receive a pacing signal;
         receive an enhanced mode signal, wherein the enhanced mode signal configures the pulse voltage regulator to switch between a first operating mode and a second operating mode;
         generate at least some of the cardiac pacing pulses at an output of the pulse voltage regulator according to the pacing signal; and
         receive a supply voltage to generate the at least some of the cardiac pacing pulses; and
      routing circuitry configured to:
      route the output of the pulse voltage regulator to the pacing output node of the pulse generator while the pulse generator is in the first operating mode; and
      route the supply voltage, gated by the pacing signal, to generate gated cardiac pacing pulses to the pacing output node of the pulse generator while the pulse generator is in the second operating mode, wherein the cardiac pacing pulses provided by the pacing output node of the pulse generator have a first voltage level when the pulse regulator is set to the first operating mode and the gated cardiac pacing pulses have a second voltage level when the pulse regulator is set to the second operating mode, the first voltage level being lower than the second voltage level.

2. The implantable cardiac stimulation device of claim 1, further comprising a battery, wherein the battery is configured to generate the supply voltage, the supply voltage being directly proportional to a voltage of the battery.

3. The implantable cardiac stimulation device of claim 1, further comprising:
a telemetry circuit configured to receive a wireless signal from an external device, the wireless signal indicating a selection of the first operating mode or the second operating mode; and
a microcontroller configured to:
receive the wireless signal indicating a selection of the first operating mode or the second operating mode from the telemetry circuit; and
generate an enhanced mode signal when the wireless signal indicates a selection of the second operating mode.

4. The implantable cardiac stimulation device of claim 1, wherein the enhanced mode signal configures the pulse voltage regulator to switch between the first operating mode and the second operating mode when the implantable cardiac stimulation device is in the presence of a high-energy radio frequency (RF) signal.

5. An implantable cardiac stimulation device for stimulating a heart of a patient, the implantable cardiac stimulation device comprising:
a pulse generator comprising:
a pacing output node configured to provide cardiac pacing pulses to the heart of the patient;
a pulse voltage regulator configured to:
receive a pacing signal;
receive an enhanced mode signal, wherein the enhanced mode signal configures the pulse voltage regulator to switch between a first operating mode and a second operating mode;
generate at least some of the cardiac pacing pulses at an output of the pulse voltage regulator according to the pacing signal; and
receive a supply voltage to generate the at least some of the cardiac pacing pulses; and
routing circuitry configured to:
route the output of the pulse voltage regulator to the pacing output node of the pulse generator while the pulse generator is in the first operating mode; and
route the supply voltage, gated by the pacing signal, to the pacing output node of the pulse generator while the pulse generator is in the second operating mode;
a voltage supply configured to generate the supply voltage and a microcontroller configured to generate the enhanced mode signal, wherein the routing circuitry comprises:
an AND gate circuit configured to be responsive to the enhanced mode signal and to an absence of the enhanced mode signal to produce an output;
an inverter circuit configured to be responsive to the enhanced mode signal and to the absence of the enhanced mode signal to produce an output;
a first switch disposed between the voltage supply and the pacing output node and responsive to the output of the AND gate; and
a second switch disposed between the pulse voltage regulator and the pacing output node and responsive to the output of the inverter circuit.

6. The implantable cardiac stimulation device of claim 5, wherein the AND gate circuit is configured to produce a low output in the absence of the enhanced mode signal so as to open the first switch.

7. The implantable cardiac stimulation device of claim 5, wherein the output of the inverter circuit is configured to close the second switch in the absence of the enhanced mode signal so as to connect the pulse voltage regulator to the pacing output node to produce a pacing pulse based on the pacing signal.

8. The implantable cardiac stimulation device of claim 5, wherein the output of the inverter circuit is configured to close the second switch in the absence of the enhanced mode signal so as to connect the pulse voltage regulator to the pacing output node to produce a pacing pulse based on a voltage of the pacing signal.

9. The implantable cardiac stimulation device of claim 5, wherein the inverter circuit is configured to open the second switch in response to the enhanced mode signal so as to disconnect the pulse voltage regulator from the pacing output node during a pulse of the pacing signal.

10. The implantable cardiac stimulation device of claim 5, wherein the AND gate circuit is configured to close the first switch in response to the enhanced mode signal so as to connect the voltage supply to the pacing output node during a pulse of the pacing signal to pass the supply voltage to the pacing output node and gate the supply voltage using the pacing signal.

11. A pulse generator for an implantable cardiac stimulation device to stimulate a heart of a patient, the pulse generator configured to switch between a first operating mode and a second operating mode, the pulse generator comprising:
a pacing output node configured to apply cardiac pacing pulses to the heart of the patient;
a voltage supply configured to provide a supply voltage;
a pulse voltage regulator configured to:
receive a pacing signal;
generate at least some of the cardiac pacing pulses at an output of the pulse voltage regulator according to the pacing signal; and
receive the supply voltage from the voltage supply to generate the at least some of the cardiac pacing pulses; and
routing circuitry configured to:
route the output of the pulse voltage regulator to the pacing output node of the pulse generator while the pulse generator is in the first operating mode; and
route the supply voltage, gated by the pacing signal, to generate gated cardiac pacing pulses to the pacing output node of the pulse generator while the pulse generator is in the second operating mode, wherein the cardiac pacing pulses applied by the pacing output node of the pulse generator have a first voltage level when the pulse generator is set to the first operating mode and the gated cardiac pacing pulses have a second voltage level when the pulse generator is set to the second operating mode, the first voltage level being lower than the second voltage level.

12. The pulse generator of claim 11, wherein the routing circuitry comprises an electrically controllable switch configured to connect the output of the pulse voltage regulator to the pacing output node of the pulse generator while the pulse generator is in the first operating mode.

13. The pulse generator of claim 11, wherein the routing circuitry comprises an electrically controllable switch configured to connect the voltage supply to the pacing output node to gate the supply voltage using the pacing signal, while the pulse generator is in the second operating mode.

14. The pulse generator of claim 11, further comprising a mode input configured to receive an enhanced mode signal, wherein the state of the enhanced mode signal determines whether the pulse generator is in the first operating mode or the second operating mode.

15. The pulse generator of claim 11, wherein the pulse generator is configured to generate the gated cardiac pacing pulses that are not attenuated or canceled when a high-energy radio frequency (RF) signal is applied to the pulse generator while the pulse generator is in the second operating mode.

16. A method for operating a pulse generator of an implantable stimulation device for stimulating a heart of a patient, the method comprising:
   generating an enhanced mode signal, wherein the enhanced mode signal configures a pulse voltage regulator to switch between a first operating mode and a second operating mode;
   determining a current operating mode of the pulse generator based on the state of the enhanced mode signal;
   receiving a pacing signal;
   when the current operating mode is the first operating mode:
      using the pulse voltage regulator of the pulse generator to generate cardiac pacing pulses at an output of the pulse voltage regulator according to the pacing signal;
      routing the output of the pulse voltage regulator to a pacing output node of the pulse generator; and
      applying the cardiac pacing pulses to the heart of the patient using the pacing output node of the pulse generator; and
   when the current operating mode is the second operating mode:
      routing a supply voltage, gated by the pacing signal, to generate gated cardiac pacing pulses to the pacing output node for application to the heart of the patient; and
      applying the gated cardiac pacing pulses to the heart of the patient using the pacing output node of the pulse generator; and wherein a voltage level of the gated cardiac pacing pulses generated during the second operating mode is higher than the voltage level of the cardiac pacing pulses generated during the first operating mode.

17. The method of claim 16, wherein routing the output of the pulse voltage regulator to the pacing output node of the pulse generator comprises:
   opening a first switch disposed between the supply voltage and the pacing output node using the output of an AND gate circuit; and
   closing a second switch disposed between the pulse voltage regulator and the pacing output node using an output of an inverter circuit so as to connect the pulse voltage regulator to the pacing output node.

18. The method of claim 16, wherein routing the supply voltage, gated by the pacing signal, to the pacing output node for application to the heart of the patient comprises:
   closing a first switch using an AND gate circuit so as to connect the supply voltage to the pacing output node during a pulse of the pacing signal; and
   opening a second switch using an inverter circuit so as to disconnect the pulse voltage regulator from the pacing output node.

19. The method of claim 16, further comprising receiving one or more wireless signals from an external device using a telemetry circuit of the implantable stimulation device to set the current operating mode.

20. The method of claim 19, wherein determining a current operating mode of the pulse generator based on the state of the enhanced mode signal comprises selecting an enhanced mode when the implantable stimulation device is in a high-energy radio-frequency (RF) environment.

* * * * *